United States Patent [19]

Brugel

[11] Patent Number: 5,891,985
[45] Date of Patent: Apr. 6, 1999

[54] SOLUBLE MONO-ALKYL STANNOIC ACID CATALYST AND ITS USE IN PREPARING HIGH MOLECULAR WEIGHT POLYESTERS

[75] Inventor: Edward Gus Brugel, Wilmington, Del.

[73] Assignee: E. I. du Pont de Nemours and Company, Wilmington, Del.

[21] Appl. No.: 942,116

[22] Filed: Oct. 1, 1997

Related U.S. Application Data

[60] Provisional application No. 60/027,932 Oct. 9, 1996.

[51] Int. Cl.$^6$ ............................. C08G 63/78; B01J 31/00
[52] U.S. Cl. ......................... 528/283; 528/271; 528/279; 528/285; 528/308; 528/308.6; 524/783; 524/784; 502/102; 502/150; 502/170; 502/172
[58] Field of Search .................................. 528/271, 279, 528/283, 285, 308, 308.6; 524/783, 784; 502/102, 150, 170, 172

[56] References Cited

U.S. PATENT DOCUMENTS

| | | | |
|---|---|---|---|
| 4,014,858 | 3/1977 | Chipman et al. | 260/75 R |
| 5,153,164 | 10/1992 | Mason | 502/324 |
| 5,162,488 | 11/1992 | Mason | 528/275 |
| 5,416,187 | 5/1995 | Kuo et al. | 528/206 |
| 5,663,281 | 9/1997 | Brugel | 528/272 |
| 5,686,218 | 11/1997 | Liebermann et al. | 430/109 |

*Primary Examiner*—Samuel A. Acquah

[57] ABSTRACT

A soluble mono-alkyl Stannoic Acid/glycol liquid phase catalyst produced from the reaction of a mono-alkyl Stannoic Acid and a glycol at a temperature of from at least 180° C., and its use in preparing high molecular weight polyester polymers.

12 Claims, No Drawings

SOLUBLE MONO-ALKYL STANNOIC ACID CATALYST AND ITS USE IN PREPARING HIGH MOLECULAR WEIGHT POLYESTERS

This application claims the benefit of U.S. Provisional Application Ser. No. 60/027,932, filed Oct. 9, 1996.

BACKGROUND OF THE INVENTION

The present invention relates to a new soluble mono-alkyl Stannoic Acid catalyst and its use in preparing high molecular weight polyester polymers. More particularly, the present invention relates to the discovery that the catalytic activity of a mono-alkyl Stannoic Acid of the type typically used in (trans) esterification reactions for preparing high molecular weight polyester polymers can be dramatically increased by pre-reacting the catalyst with an alkylene glycol.

U.S. Pat. No. 4,014,858 describes a first stage polyesterification for the preparation of polybutylene terephthalate which proceeds by reacting in the presence of an organotin catalyst having one organo to each tin linkage (1) a polycarboxylic acid compound (acid, anhydride and/or methyl ester) comprising terephthalic acid in a concentration of at least 50 equivalent percent of the carboxy equivalents and (2) a polyhydric alcohol component comprising from 75 to 100 equivalent percent 1,4-butanediol with the polyhydric alcohol being present in a concentration of from 1.1 to 4 hydroxy equivalents per carboxyl equivalent. The organotin catalyst can be a hydrocarbyl Stannoic Acid having the structure:

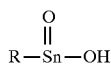

wherein each R contains from 1 to 24 carbon atoms and can be alkyl or cycloalkyl. It is noted that since the organotin catalyst can be heated with 1,4-butanediol without the formation of tetrahydrofuran, the polyhydric alcohol component and catalyst can be preheated to the initial reaction temperature, i.e., 165° C. to 170° C., and the preheated polyhydric alcohol composition can then be introduced into the reactor with the other reactants.

SUMMARY OF THE INVENTION

The present invention relates to a new soluble mono-alkyl Stannoic Acid catalyst which is formed by heating, i.e., reacting, a mono-alkyl Stannoic Acid, and, in particular, mono-butyl Stannoic Acid, with a glycol of the formula (I):

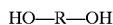 (I)

wherein R is selected from $C_2$ to $C_{50}$ alkyl, cycloalkyl, aryl and combinations thereof, at a temperature of at least 180° C., preferably greater than about 200° C., and most preferred in the range of from 200° C. to 210° C., whereby the mono-alkyl Stannoic Acid reacts selectively with the glycol to yield a mono-alkyl Stannoic Acid/glycol liquid phase and, under some conditions, a solid precipitate. The mono-alkyl Stannoic Acid/glycol liquid phase demonstrates substantially improved catalytic activity as an esterification catalyst when compared to unreacted mono-alkyl Stannoic Acid.

According to another aspect, the present invention is an improvement in a process for preparing high molecular weight polyester polymers, such as polyethylene terephthalate (PET), polypropylene terephthalate (PPT), and polybutylene terephthalate (PBT), which process includes esterifying one or more mono-, di- or tricarboxylic acids and one or more alkyl(aryl) glycols in the presence of an esterification catalyst, the improvement comprising esterifying said one or more mono-, di- or tricarboxylic acids and said one or more alkyl(aryl) glycols in the presence of a mono-alkyl Stannoic Acid/glycol liquid phase catalyst which is produced by reacting a mono-alkyl Stannoic Acid with an alkyl(aryl) glycol at a temperature greater than 180° C., preferably greater than 200° C., and most preferred in the range of from 200° C. to 210° C., and at a glycol:tin ratio in the range of from 3:1 to about 1000:1 by weight. The reaction may also be characterized by the formation of a solid precipitate as a reaction by-product which, optionally, can be removed. In either case, the resulting mono-alkyl Stannoic Acid/glycol liquid phase can be added directly to the (trans)esterification reaction mixture as the catalyst, or, as an alternative, the mono-, di- or tricarboxylic acid component of the reaction can be added directly to the mono-alkyl Stannoic Acid/glycol liquid phase.

According to one embodiment of the invention, the glycol reactant, in which the mono-alkyl Stannoic Acid is heated to produce the mono-alkyl Stannoic Acid/glycol liquid phase catalyst, corresponds to the alkyl(aryl) glycol portion of the high molecular weight polyester polymer being produced, although this correspondence has not been observed to be a limitation of the utility for the new mono-alkyl Stannoic Acid/glycol liquid phase catalyst. The new catalyst can be employed in any (trans)esterification reaction of a mono-, di- or tricarboxylic acid and an alkyl(aryl) glycol.

According to another aspect, the present invention is a method for preparing a mono-alkyl Stannoic Acid/glycol soluble catalyst which comprises heating a mono-alkyl Stannoic Acid selected from mono-butyl Stannoic Acid and mono-octyl Stannoic Acid in the presence of a glycol to a temperature greater than 180° C., preferably greater than 200° C., and most preferred in the range of from 200° C. to 210° C., to yield the corresponding mono-alkyl Stannoic Acid/glycol liquid phase optionally, the mono-alkyl Stannoic Acid/glycol liquid phase can be further refined by removing any precipitate which may be present in the liquid phase. The improved mono-alkyl Stannoic Acid/glycol soluble catalyst demonstrates excellent thermal stability. It significantly reduces esterification reaction time, i.e., time to "clear" solution, and improves production of high molecular weight polymer by either melt polycondensation or solid-state polycondensation methods.

DETAILED DESCRIPTION

The present invention resides in the discovery that in first stage polyesterification which takes place, for example, in a reaction between terephthalic acid and an alkyl(aryl) glycol, e.g., 1,4-butanediol, in the presence of a catalytic concentration of a mono-alkyl Stannoic Acid, the catalytic activity of the mono-alkyl Stannoic Acid is substantially increased by pre-reacting the catalyst with the glycol, i.e., heating the mono-alkyl Stannoic Acid with the glycol at a glycol:tin ratio of from 3:1 to about 1000:1, by weight, at a temperature which is at least 180° C., preferably at a temperature greater than 200° C., and most preferred at a temperature in the range of from 200° C. to 210° C., to thereby produce a mono-alkyl Stannoic Acid/glycol liquid phase. The reaction may also be characterized by the formation of a solid reaction by-product(s) as a precipitate, which can optionally be removed from the liquid phase by filtering or by any other convenient solid/liquid separation means. The mono-alkyl Stannoic Acid/glycol liquid phase can then be introduced as the catalyst directly into the (trans)esterification reaction mixture.

Although the initial discovery of increased catalytic activity for the mono-alkyl Stannoic Acid/glycol liquid phase catalyst as discussed above occurred in connection with first stage polyesterification in a process for the production of low molecular weight pre-polymers, increased catalytic activity has also been observed in connection with solid state polymerization of such pre-polymers to high molecular weight without formation of undesirable sublimate. Beyond this, the catalytic activity of the mono-alkyl Stannoic Acid/glycol liquid phase catalyst has not been observed to decrease during melt finishing.

The molecular structure of the tin species formed within the glycol liquid phase has not been identified, but the results of Ethyl Grignard Derivatization followed by GC/MS analysis suggest that at least a portion of the mono-alkyl Stannoic Acid starting compound is selectively reacted, i.e., it disproportionates or structurally rearranges in the presence of the glycol at elevated temperatures, to yield dialkyltin and trialkyl tin structures. The solid precipitate is primarily inorganic tin.

In carrying out the invention, a mono-alkyl Stannoic Acid is heated with a glycol as defined above to a reaction temperature of at least 180° C., whereby the tin compound reacts selectively with the glycol. As is well known to those skilled in the art, the reaction temperature will depend primarily on the selected glycol reactant. Accordingly, the reaction temperature can range from a temperature as low as 180° C. up to a temperature as high as 240° C., or even higher. When the glycol is an alkylene glycol of the formula $OH(CH_2)_nOH$, where n is from 2 to 20, for example, the reaction temperature will typically be in the range of from 200° C. to 210° C.

The new highly active mono-alkyl Stannoic Acid catalyst remains soluble in the glycol, and in that form unexpectedly exhibits substantially greater overall catalytic activity in producing high molecular weight polyester polymers than unreacted mono-alkyl Stannoic Acid. Another important benefit achievable with the new mono-alkyl Stannoic Acid catalyst of the invention is less undesirable by-product formation during (trans)esterification, meaning that there is a higher conversion of the carboxylic acid ends during (trans)esterification than is obtainable using a typical unreacted mono-alkyl Stannoic Acid catalyst. The catalytic activity of the mono-alkyl Stannoic Acid/glycol liquid phase catalyst is sufficiently high that polymerization to high molecular weight during polycondensation can usually be achieved without further addition of catalyst. However, additional mono-alkyl Stannoic Acid/glycol liquid phase catalyst may be added after (trans)esterification and/or for polycondensation. In addition, the mono-alkyl Stannoic Acid/glycol liquid phase catalyst of the invention may also be used at any stage of the (trans)esterification-polycondensation reaction sequence in combination with one or more conventional catalysts selected from the group consisting of unreacted tin compounds, such as, dibutyl-tin oxide and monobutyl-tin oxide chloride; antimony oxide; antimony glycolates; titanates; germanium oxides; and the like.

In carrying out the invention according to a preferred embodiment, the mono-alkyl Stannoic Acid, preferably mono-butyl Stannoic Acid, and the alkyl(aryl) glycol, preferably an alkylene glycol selected from the group consisting of $OH(CH_2)_nOH$ where n is from 2 to 20, are charged to a stirred reactor, and the temperature of the reactor increased to 205° C. The reactor is then maintained at a temperature of from 205° C. to 210° C. for an additional 1 to 10 hours depending on the chemical structure of the glycol and its ability to react with the mono-alkyl Stannoic Acid. During this time water may be distilled off via a distillation head and collected. After the selected time period, the reactor is allowed to cool to ambient temperature. The reaction is characterized by the formation of a solid precipitate, which can be removed by filtering, although a separate cool-down step and removal of the precipitate are not necessary.

The reaction product is a mono-alkyl Stannoic Acid/glycol liquid phase, which can then be added to a (trans) esterification reactor that contains the alkyl(aryl) glycol(s) and the mono-, di- or tricarboxylic acid(s) in appropriate reaction amounts usually at an initial temperature of about 180° C. As noted above, according to one embodiment for carrying out the invention, the mono-alkyl Stannoic Acid/glycol liquid phase can be added directly to the (trans) esterification reactor without first providing for a separate cool-down step. In either case, after addition, the reactor temperature is adjusted to from 180° C. to about 225° C. and maintained at that temperature for about 2 hours. During that time, undesirable by-products, such as, for example, tetrahydrofuran, and excess glycol, are distilled off. Near the end of this reaction time period the reaction mixture will usually turn from opaque to clear, and this will indicate that the (trans)esterification of the acid end groups is near completion. The reaction mixture can then be cooled to ambient, i.e., room, temperature, and the acid end group concentration can be determined.

When compared to prior art methods of adding the respective reactants and unreacted mono-alkyl mono-alkyl Stannoic Acid catalyst individually to the reactor at the beginning of the process, all other factors being equal, the instant reaction can reach completion in less than 60 minutes, and the concentration of acid end groups in the reaction mixture at completion will generally be in the range of, and sometimes less than, 100 meg/Kg, i.e., at least about one-half the concentration observed in the corresponding prior art reaction mixture. In addition, it has also been observed that as the concentration of mono-alkyl Stannoic Acid/glycol liquid phase catalyst is increased, other factors being constant, the rate of reaction, i.e., the rate at which the carboxylic acid goes into solution, also increases.

The esterified generally low molecular weight polymer can be converted to high molecular weight, i.e., polymerized, by any suitable melt finishing means, such as, for example, solid state polymerization (SSP). When solid state polymerization is used to polymerize low molecular weight polyester polymers produced using the mono-alkyl Stannoic Acid/glycol (trans)esterification catalyst of the invention, the solid state reaction rate is increased over the rate obtained according to the prior art, and the formation of sublimate, i.e., objectionable cyclic oligomer, during solid state polymerization is substantially reduced and usually avoided.

The process of the invention can be used with good results where the high molecular weight polymer to be produced is a polycarbonate. In that instance, the mono-alkyl Stannoic Acid/glycol liquid phase catalyst, preferably derived from mono-butyl Stannoic Acid, and Bisphenol A are reacted with a dialkyl and/or diaryl carbonate, such as, for example, diphenyl carbonate or dimethyl carbonate. Where the desired high molecular weight polymer is a liquid crystal polymer (LCP), the starting glycol from which the mono-alkyl Stannoic Acid/glycol liquid phase catalyst is to be produced will be selected from aromatic glycols, such as, for example, hydroquinone, or from hydroxy acids, such as hydroxy benzoic acid.

EXAMPLES

In the examples which follow, mono-butyl Stannoic Acid has been selected to illustrate the invention. Mono-alkyl Stannoic Acids for use according to the invention can be prepared by the hydrolysis of their corresponding mono-alkyl tin trichlorides according to published procedures well known in the art, but for convenience the mono-alkyl Stannoic Acids can be obtained commercially from WITCO Corporation, Greenwich, Conn. 06831.

Preparation of Catalyst 250 grams of 1,4-butanediol and 15 grams of mono-butyl Stannoic Acid were charged to a 500 ml resin kettle fitted with an agitator and distillation head. The temperature of the reaction mixture was increased to 205° C. At 205° C. the solution became clear, and the mixture was held between 205° C. and 210° C. for an additional two hours. The mixture was then allowed to cool overnight to allow for precipitation, and then it was filtered. Thermogravimetric analysis of the liquid showed 2.73% ash.

Esterification Reaction

A 2-liter reaction kettle fitted with an agitator and distillation head was charged with 800 grams of terephthalic acid, 485 grams of 1,4-butanediol and 100 grams of the glycol/catalyst solution. The reaction mixture was then heated to 220° C. while water and small amounts of tetrahydrofuran and excess 1,4-butanediol were removed. After one hour the reaction mixture had cleared and the temperature was increased to 230° C. and held for 2 hours. The mixture was then allowed to cool, and analysis for carboxylic end groups by titration found 114 meg/Kg.

A second experiment using the same starting materials, i.e., terephthalic acid and 1,4-butanediol, in the same respective amounts, was conducted for comparison in which the catalyst was unreacted mono-butyl Stannoic Acid. After 3 hours the reaction was terminated. The reaction mixture had not turned clear, and the final carboxylic acid content of the reaction mass was 407 meg/Kg.

Representative tin catalysts which can be used in practicing the invention include the following:
mono-methyl Stannoic Acid
mono-ethyl Stannoic Acid
mono-n-propyl Stannoic Acid
mono-n-butyl Stannoic Acid (monobutyl Stannoic Acid, i.e., MBSA, and sometimes referred to as mono-butyl tin oxide)
mono-n-pentyl Stannoic Acid
mono-n-hexyl Stannoic Acid
mono-2-butyl Stannoic Acid
mono-i-butyl Stannoic Acid
mono-t-butyl Stannoic Acid
mono-i-propyl Stannoic Acid
mono-cyclohexyl Stannoic Acid Representative glycols which can be used in practicing the invention include the following:
1,2-ethanediol
1,3-propanediol
1,2-propanediol
1,4-butanediol
1,2-butanediol
1,5-pentanediol
1,6-hexanediol
1,8-octanediol
1,10-decanediol
1,12-dodecanediol
cyclohexane-1,4-diol
cyclohexane-1,3-diol
cyclohexane-1,2-diol
1,4-dioxymethylcyclohexane
4,4'-dihydroxybiphenyl
hydroquinone
methyl-1,4-hydroquinone
methylhydroquinone
tert.-butylhydroquinone
chlorohydroquinone
phenylhydroquione
1,2,4-butane triol
4,4'-isopropylidenediphenol (Bisphenol A)
4,4'-dihydroxy biphenyl (Biphenol)
2,6-dihydroxy naphthalene
2,3-dihydroxy naphthalene
1,6-dihydroxy naphthalene
bis(4-hydroxyphenyl)ether
1,4-dihydroxynaphthalene
2,2-bis-(4-hydroxyphenyl)-pentane
2,4'-dihydroxy diphenyl methane
bis-(2-hydroxyphenyl) methane
bis-(4-hydroxyphenyl)-methane
1,1-bis-(4-hydroxyphenyl)-ethane
3,3-bis-(4-hydroxyphenyl)-pentane
2,2-bis(3,5-dibromo-4-hydroxyphenyl)propane ("Tetrabromo Bisphenol-A" or "TBBA")
2,2-bis(3,5-dimethyl-4-hydroxyphenyl)propane ("Tetramethyl Bisphenol-A")
bis(4-hydroxy-5-nitrophenyl)-methane 1-bis(4-hydroxyphenyl)-1-phenyl ethane ("Bisphenol-AP" or "Bis-AP")
9,9-bis(4-hydroxyphenyl)fluorene ("BHPF")
1,1-bis(4-hydroxyphenyl)cyclohexane
resorcinol
bis-(4-hydroxyphenyl) sulfone
2,4'-dihydroxydiphenyl sulfone
5'-chloro-2,4'-dihydroxydiphenyl sulfone, bis-(4-hydroxyphenyl) diphenyl disulfone
4,4'-dihydroxydiphenyl ether
4,4'-dihydroxy-3,3'-dichloro diphenyl ether
4,4'-dihydroxy-2,5-diethoxydiphenyl ether
diethylene glycol
dimethylbutanediol
hydrogenated bisphenol A
glycerol
sorbitol
neopentyl glycol
2-methyl-1,3-propanediol
1,2,6-hexanetriol
trimethylolethane
trimethylolpropane
pentaerythritol
  quinitol
  mannitol
  dipentaerythritol Of the foregoing glycols, 1,2-ethanediol, 1,3-propanediol and 1,4-butanediol are preferred because of their commercial availability and utility.

Among the dicarboxylic acids which are operable in practicing the invention are the following:
terephthalic acid
isophthalic acid
2,6-naphthalene dicarboxylic acid
2,7-naphthalene dicarboxylic acid
methoxyterephthalic acid
ethoxyterephthalic acid
fluoroterephthalic acid
chloroterephthalic acid
bromoterephthalic acid
methylterephthalic acid
methoxyisophthalic acid
biphenyl-4,4'-dicarboxylic acid diphenylether-4,4'-dicarboxylic acid
naphthalene-2,6-dicarboxylic acid
naphthalene-1,5-dicarboxylic acid
naphthalene-1,4-dicarboxylic acid
succinic acid
adipic acid
azelaic acid
sebacic acid
decamethylenedicarboxylic
phthalic acid
trimellitic acid
pyromellitic acid
tetrahydrophthalic acid
hexahydrophthalic acid Representative of mixed alcohols and acids which can be used according to the invention are the following:
4-hydroxy benzoic acid
4-hydroxy-3-chlorobenzoic acid
4-hydroxy-3-methylbenzoic acid
m-hydroxybenzoic acid
4-hydroxy-3,5-dimethylbenzoic acid
2-hydroxy-6-naphthoic acid
1-hydroxy-5-naphthoic acid
1-hydroxy-4-naphthoic acid Examples of esters which can be used according to the invention are the following:
Dimethyl Terephthalate
Dimethyl Isophthalate
Dimethyl Phthalate
bis(2-hydroxyethyl) terephthalate
bis (3-hydroxypropyl) terephthalate
bis (4-hydroxybutyl) terephthalate
bis (2-hydroxyethyl) naphthalenedioate
bis (2-hydroxyethyl) isophthalate
bis [2-(2-hydroxyethoxy) ethyl] terephthalate
bis [2-(2-hydroxyethoxy) ethyl] isophthalate
bis [(4-hydroxymethylcyclohexyl)methyl] terephthalate
bis [(4-hydroxymethylcyclohexyl)methyl] isophthalate The Mono-alkyl Stannoic Acid/glycol liquid phase catalyst and the process of the invention are particularly useful in preparing the following high molecular weight polymers:
poly(ethylene terephthalate), i.e., PET or 2GT
poly(1,3-propylene terephthalate), i.e., PPT or 3GT
poly(1,4-butylene terephthalate), i.e., PBT or 4GT
poly(ethylene naphthalenedioate)
poly(ethylene isophthalate)
poly(3-oxa-1,5-pentadiyl terephthalate)
poly(3-oxa-1,5-pentadiyl isophthalate)
poly[1,4-bis(oxymethyl)cyclohexyl terephthalate]
poly[1,4-bis(oxymethyl)cyclohexyl isophthalate]

The foregoing examples and the listed reactants for carrying out the invention are merely illustrative and should not be construed as limiting the scope of the invention.

What is claimed is:

1. A soluble mono-alkyl Stannoic Acid catalyst which is formed by heating a mono-alkyl Stannoic Acid with a glycol of the formula (I):

HO—R—OH    (I)

wherein R is selected from $C_2$ to $C_{50}$ alkyl, cycloalkyl, aryl and combinations thereof at a temperature of at least 180° C. whereby the mono-alkyl Stannoic Acid is selectively reacted with the glycol to yield a mono-alkyl Stannoic Acid/glycol liquid phase.

2. The soluble mono-alkyl Stannoic Acid catalyst of claim 1 in which the mono-alkyl Stannoic Acid and the glycol are heated to a temperature in the range of from 200° C. to 210° C.

3. In a process for preparing a high molecular weight polyester polymer from a low molecular weight reaction product obtained from (trans)esterifying one or more mono-, di- or tricarboxylic acids and one or more alkyl(aryl) glycols in the presence of a (trans)esterification catalyst, the improvement comprising (trans)esterifying said one or more mono-, di- or tricarboxylic acids and said one or more alkyl(aryl) glycols in the presence of a mono-alkyl Stannoic Acid/glycol liquid phase catalyst which is produced by reacting a mono-alkyl Stannoic Acid with an alkyl(aryl) glycol at a temperature in the range of at least 180° C. at a glycol:tin ratio in the range of from 3:1 to 1000:1 by weight.

4. The improvement according to claim 3 wherein the (trans)esterification catalyst further comprises a conventional catalyst selected from the group consisting of unreacted tin compounds, antimony oxide, antimony glycolates, titanates, germanium compounds and combinations thereof.

5. The improvement according to claim 4 wherein the glycol reactant in which the mono-alkyl Stannoic Acid is heated to produce the mono-alkyl Stannoic Acid/glycol catalyst corresponds to the alkyl(aryl) glycol portion of the high molecular weight polyester polymer reaction product.

6. The improvement according to claim 5 in which the one or more mono-, di- or tricarboxylic acids is a dicarboxylic acid selected from terephthalic acid and isophthalic acid; the mono-alkyl Stannoic Acid is mono-butyl Stannoic Acid; and the alkyl(aryl) glycol is a diol selected from 1,2-ethane diol, 1,3-propane diol and 1,4-propane diol.

7. The improvement according to claim 6 in which the mono-butyl Stannoic Acid and the diol are reacted at a temperature in the range of from 200° C. to 210° C.

8. A method for preparing a mono-alkyl Stannoic Acid/glycol soluble catalyst which comprises:
(a) heating a mono-alkyl Stannoic Acid selected from mono-butyl Stannoic Acid and mono-octyl Stannoic Acid in the presence of a glycol to a temperature of at least 180° C. until the starting tin compound is selectively reacted with the glycol;
(b) allowing the reaction mixture to cool to yield a mono-alkyl Stannoic Acid/glycol liquid phase and a solid precipitate; and optionally
(c) removing the solid precipitate from the mono-alkyl Stannoic Acid/glycol liquid phase.

9. The method of claim 8 in which the mono-alkyl Stannoic Acid and the glycol are heated to a temperature in the range of from 200° C. to 210° C.

10. A process for preparing a high molecular weight polyester polymer selected from poly(ethylene terephthalate), poly(1,3-propylene terephthalate) and poly (1,4-butylene terephthalate) which comprises:
(a) (trans)esterifying a dicarboxylic acid selected from terephthalic acid and isothalaic acid with a glycol selected from 1,2-ethanediol, 1,3-propanediol and 1,4-butanediol in the presence of a (trans)esterification catalyst which is a mono-alkyl Stannoic Acid/glycol liquid phase catalyst which is produced by reacting a mono-alkyl Stannoic Acid with a glycol selected from 1,2-ethanediol, 1,3-propanediol and 1,4-butanediol at a temperature in the range of from 200° C. to 210° C. at a tin:glycol ratio in the range of from 3:1 to 1000:1 by weight to produce a low molecular weight pre-polymer, and
(b) polymerizing the pre-polymer to high molecular weight in a meltpolycondensation reaction or by solid state polymerization.

11. The process of claim 10 in which the (trans) esterification catalyst further comprises a conventional catalyst selected from the group consisting of unreacted tin compounds, antimony oxide, antimony glycolates, titanates, germanium oxides and combinations thereof.

12. The process of claim 11 in which polymerization to high molecular weight according to step (b) is carried out by introducing for step (b) a polymerization catalyst selected from the group consisting of a mono-alkyl Stannoic Acid/glycol liquid catalyst, unreacted tin compounds, antimony oxide, antimony glycolates, titanates, germanium oxides, and combinations thereof.

* * * * *